United States Patent
Van Gompel et al.

(10) Patent No.: US 7,201,744 B2
(45) Date of Patent: Apr. 10, 2007

(54) REFASTENABLE ABSORBENT GARMENT AND METHOD FOR ASSEMBLY THEREOF

(75) Inventors: Paul T. Van Gompel, Hortonville, WI (US); Yung H. Huang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 782 days.

(21) Appl. No.: 10/032,700

(22) Filed: Dec. 28, 2001

(65) Prior Publication Data

US 2003/0135184 A1    Jul. 17, 2003

(51) Int. Cl.
*A61F 13/15*    (2006.01)

(52) U.S. Cl. .................. 604/391; 604/394; 604/387; 604/389; 604/396

(58) Field of Classification Search ........... 604/396, 604/387, 389, 391, 394, 386
See application file for complete search history.

(56) References Cited

U.S. PATENT DOCUMENTS

| | | | |
|---|---|---|---|
| 4,315,508 A | 2/1982 | Bolick | |
| 4,522,853 A | 6/1985 | Szonn et al. | |
| 4,537,591 A | * 8/1985 | Coates | 604/391 |
| 4,555,244 A | * 11/1985 | Buell | 604/392 |
| 4,680,030 A | * 7/1987 | Coates et al. | 604/391 |
| 4,701,170 A | * 10/1987 | Wilson et al. | 604/385.22 |
| 4,887,338 A | 12/1989 | Handler | |
| 4,895,569 A | 1/1990 | Wilson et al. | |
| 4,909,804 A | 3/1990 | Douglas, Sr. | |
| 4,972,525 A | 11/1990 | Hwang | |
| 5,019,065 A | 5/1991 | Scripps | |
| 5,074,854 A | 12/1991 | Davis | |
| 5,108,384 A | * 4/1992 | Goulait | 604/390 |
| 5,624,428 A | * 4/1997 | Sauer | 604/391 |
| 5,662,638 A | 9/1997 | Johnson et al. | |
| 5,855,574 A | 1/1999 | Kling et al. | |
| 5,858,515 A | 1/1999 | Stokes et al. | |
| 5,891,122 A | 4/1999 | Coates | |
| 5,919,334 A | 7/1999 | Niedermeyer | |
| 6,007,527 A | 12/1999 | Kawaguchi et al. | |
| 6,036,805 A | 3/2000 | McNichols | |
| 6,092,242 A | 7/2000 | Niedermeyer | |
| 6,120,489 A | 9/2000 | Johnson et al. | |
| 6,132,410 A | 10/2000 | Van Gompel et al. | |

(Continued)

FOREIGN PATENT DOCUMENTS

EP    0 570 980    11/1993

(Continued)

*Primary Examiner*—Jacqueline F. Stephens
(74) *Attorney, Agent, or Firm*—Brinks Hofer Gilson & Lione

(57) ABSTRACT

A refastenable absorbent garment includes a first body panel having a body side and a garment side and a second body panel having a body side and a garment side. A fastener member is attached to the body side of the first body panel and is releasably attached to the body side of the second body panel. A method for assembling a refastenable absorbent garment includes applying a garment side of a first portion of the fastener member to a body side of a first body panel, and releasably applying the body side of the second body panel to a garment side of a second portion of the fastener member. A method of manufacturing and using the absorbent garment is also provided.

38 Claims, 5 Drawing Sheets

U.S. PATENT DOCUMENTS

| | | |
|---|---|---|
| 6,197,138 B1 | 3/2001 | McNichols |
| 6,210,388 B1 | 4/2001 | Widlund et al. |
| 6,217,563 B1 | 4/2001 | Van Gompel et al. |
| 6,264,641 B1 | 7/2001 | Van Gompel et al. |
| 6,296,629 B1 | 10/2001 | Siebers et al. |
| 6,336,922 B1 | 1/2002 | Van Gompel et al. |
| 6,361,527 B1 | 3/2002 | Van Gompel et al. |
| 6,375,646 B1 | 4/2002 | Widlund et al. |

FOREIGN PATENT DOCUMENTS

| | | |
|---|---|---|
| EP | 0 907 510 B1 | 3/2002 |
| JP | 03176053 A | 7/1991 |
| JP | 3-205053 | 9/1991 |
| WO | WO 95/27461 | 10/1995 |
| WO | WO 95/27462 | 10/1995 |
| WO | WO 97/23180 | 7/1997 |
| WO | WO 97/28774 | 8/1997 |
| WO | WO 98/37847 | 9/1998 |
| WO | WO 00 20208 | 4/2000 |
| WO | WO 00/35395 | 6/2000 |
| WO | WO 00/35397 | 6/2000 |
| WO | WO 00/35398 | 6/2000 |
| WO | WO 01/67912 A2 | 9/2001 |
| WO | WO 01/87204 A1 | 11/2001 |
| WO | WO 01/87207 A1 | 11/2001 |

\* cited by examiner

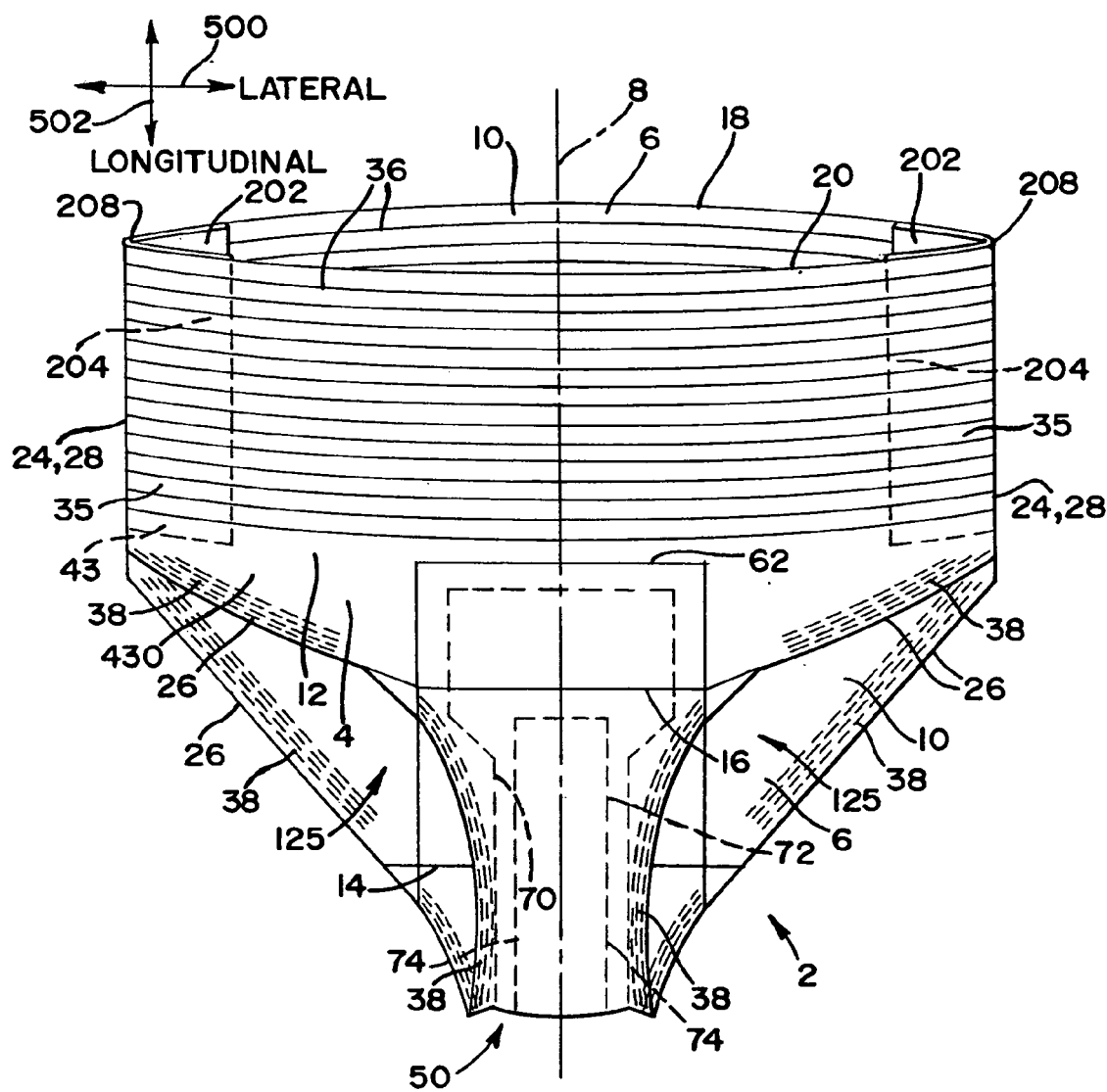

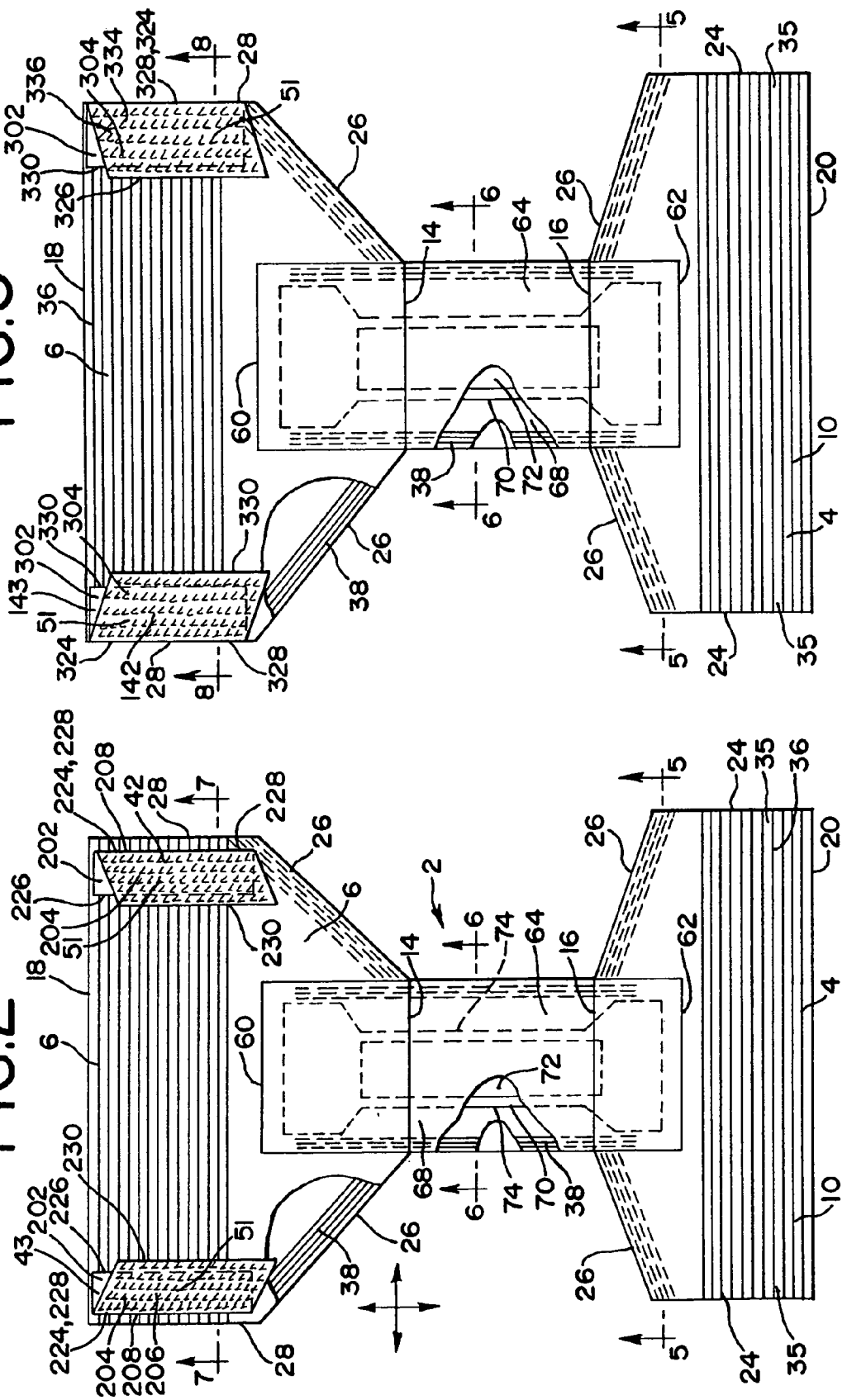

REFASTENABLE ABSORBENT GARMENT AND METHOD FOR ASSEMBLY THEREOF

BACKGROUND

The present invention relates generally to a refastenable absorbent garment, and in particular, to a seamless, pant-type refastenable absorbent garment and to a method for the fabrication thereof.

Absorbent garments can be configured in many different forms. For example, absorbent garments can be configured as a pant-type, pull-on garment, or as a diaper-type product that is drawn up between the legs and fastened about the waist with various fastening systems. Pant-type, pull-on garments are often provided with various elastic elements that can conform to the body of the user and provide a comfortable, snug fit. Such garments, however, often do not have a refastenable mechanism that allows the garment to be easily removed after use or to be adjusted during use. Rather, pant-type garments are often made from one or more body panels that are joined at a seam formed along the side of the garment.

Diaper-type products, which can be configured with fastening systems that allow the user to detach and reattach various fasteners so as to provide a refastenable absorbent garment, often are not configured with various elastic elements, for example around the waist, and may not conform well to the body of the user and/or may provide a bulky appearance beneath the user's garments. Moreover, such garments are typically produced as an "open" product, which is open at the sides and which cannot be pulled on like a pant-type garment. Some consumers prefer a pull-on type garment, since the garment is applied to the user like conventional underwear. Therefore, there remains a need for an improved absorbent garment, and in particular a pant-type garment, that is refastenable and provides a snug fit with a non-bulky appearance.

In addition, manufacturing facilities are often configured to fabricate one particular type of product. As such, these facilities may not provide the flexibility to transition between fabricating a conventional pull-on type garment with side seams and fabricating a refastenable garment using a single manufacturing line or asset. Therefore the need also remains for improved methods and assemblies for manufacturing refastenable absorbent garments.

SUMMARY

Briefly stated, in one aspect, one preferred embodiment of a refastenable absorbent garment includes a first body panel having a body side and a garment side and a second body panel having a body side and a garment side. A fastener member is attached to the body side of the first body panel and is releasably attached to the body side of the second body panel. In one preferred embodiment, the fastener member is fixedly attached to the body side of the first body panel.

In one preferred embodiment, the fastener member includes a first portion attached to the body side of the first body panel and a second portion attached to the body side of the second body panel, wherein the first and second portions are hingedly connected, preferably along an outboard edge thereof. In one preferred embodiment, the fastener member includes a first and second fold forming the first and second portions, and a folded edge forming the hinge. In an alternative preferred embodiment, the first portion is bonded to the second portion.

In another aspect, one preferred embodiment of a method for assembling a refastenable absorbent garment includes applying a garment side of a first portion of a fastener member to a body side of a first body panel, and releasably applying the body side of the second body panel to a garment side of a second portion of the fastener member.

In another aspect, one preferred embodiment of a method for manufacturing a refastenable absorbent garment includes moving a first body panel web having a body side and a garment side in a machine direction, moving a second body panel web having a body side and a garment side in a machine direction and providing a plurality of fastener members each comprising a first and second portion each having a body side and a garment side. The method further preferably includes successively applying the garment side of the first portions of the fastener members to the body side of the first body panel web, and successively, releasably applying the body side of the second body panel web to the garment side of the second portions of the fastener members. In one preferred embodiment, the method further includes fixedly securing the first portion to the body side of the first body panel, for example and without limitation by bonding. In one preferred embodiment the method further includes successively cutting the first and second body panel webs and the first and second portions to form a plurality of discrete absorbent garments.

In another aspect, a method of using the absorbent garment is also provided. The method preferably includes disconnecting the fastener member from the body side of the second body panel, and further preferably includes releasably reengaging the fastener member with the body side of the second body panel.

The presently preferred embodiments provide significant advantages over other absorbent garments and methods for the manufacture thereof. For example, in one embodiment of a pant-type garment, the user can pull the garment on or off like underwear. However, by making the absorbent garment refastenable, it can be applied without needing to pull the garment on or off like a pant-like garment, if desired. Moreover, the garment can be pulled on like a pant-type garment and removed like a diaper-type product by disengaging the fastener members. Alternatively, the garment can be pulled on and off like a pant-like garment, and can thereafter be converted to a refastenable garment, if desired. For example, the garment can be made bigger or smaller simply by adjusting the positioning of the fasteners. Moreover, in one particular application, wherein the garment is used by adults, for example with occasional incontinence problems, the garment can be pulled up or down by the user, or the fastening system may be disengaged and engaged repeatedly by the user while the garment remains unsoiled over an extended period of time.

The preferred embodiment of the garment, with the fastener members located on the body side of the body panels, provides a pleasing pant-like appearance and does not have fastener members that are visible once the garment is applied to the user. In addition, the fastening system avoids the need to overlap the first and second body panels, which overlapping can create a bulky feel and appearance beneath the user's garments. Moreover, the body panels are not required to be joined at their outboard edges at a seam, such that a manufacturing step can be eliminated. In addition, the seamless garment avoids potentially unsightly lines beneath the user's garments.

In one preferred embodiment, the absorbent garment includes elastic elements extending along the waist region. The elastic elements provide a snug, comfortable fit that does not create a bulky appearance beneath the user's outer garments. The combination of the refastenable fasteners with the elastic elements further enhances the fit and appearance of the garment.

The preferred methods for making the refastenable garment also provide significant advantages. For example, the manufacturer can easily switch between the manufacture of a non-refastenable, pant-type product having conventional seams and a refastenable product, simply by introducing a plurality of fastener pieces, applying those fastener pieces between the first and second body panels and eliminating the side seam bonder. In this way, the machinery and equipment used to fabricate the body panels and crotch portion can be integrated into both processes, thereby maximizing the use of the assets and reducing the costs and space needed for the manufacturing facility. In addition, in one preferred embodiment, the method allows the manufacturer to use the fastener member to hold the first and second body panels together in a folded configuration as they are further processed.

The foregoing paragraphs have been provided by way of general introduction, and are not intended to limit the scope of the following claims. The present invention, together with further advantages, will be best understood by reference to the following detailed description of the presently preferred embodiments taken in conjunction with the accompanying drawings.

BRIEF DESCRIPTION OF THE DRAWINGS

FIG. 1 is a front perspective view of one embodiment of a refastenable absorbent garment in a fastened configuration.

FIG. 2 is plan view of one embodiment of a refastenable absorbent garment in an unfastened configuration.

FIG. 3 is plan view of an alternative embodiment of a refastenable absorbent garment in an unfastened configuration.

DETAILED DESCRIPTION OF THE PRESENTLY PREFERRED EMBODIMENTS

Figure 4:
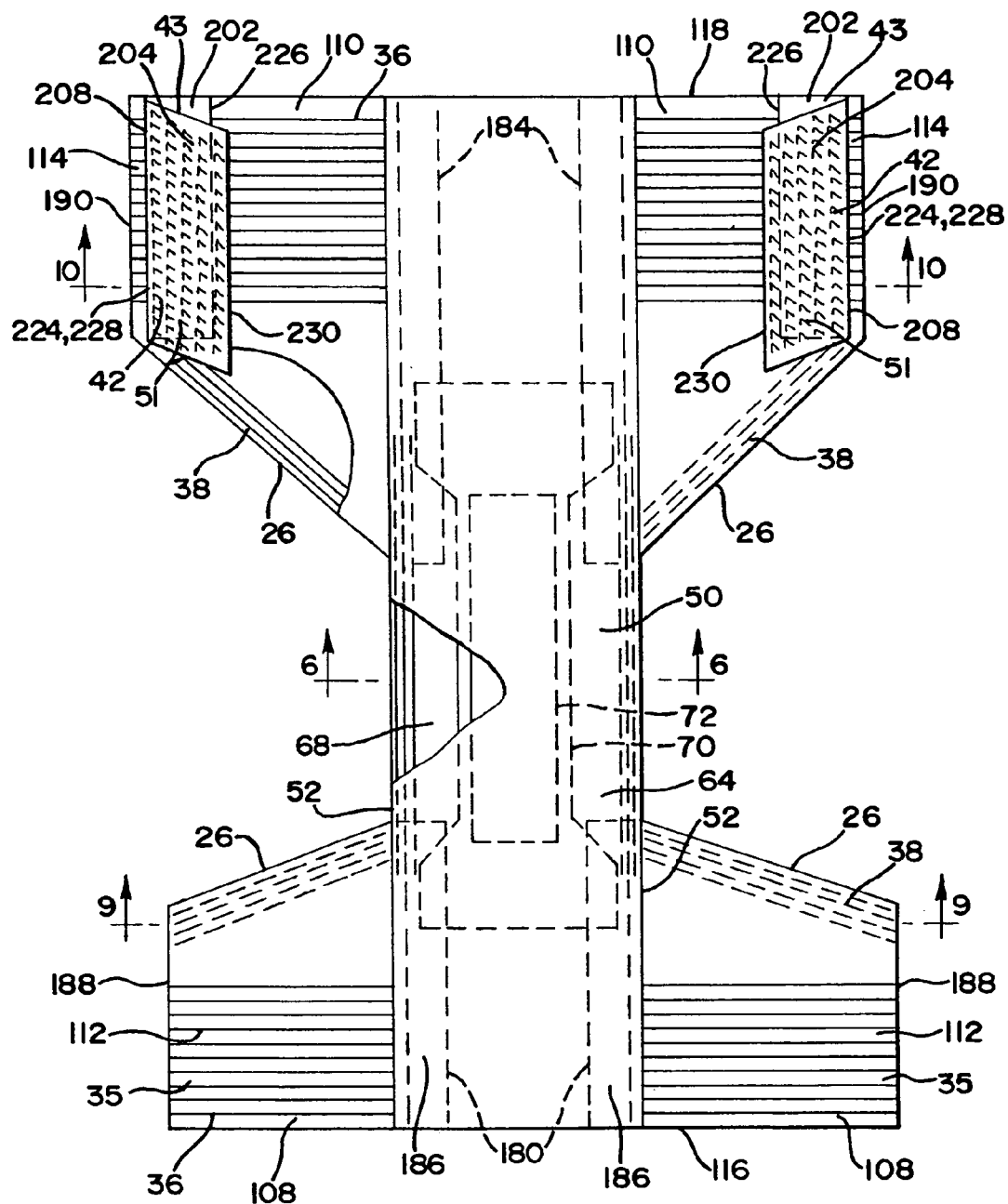
FIG. 4 is plan view of an alternative embodiment of a refastenable absorbent garment in an unfastened configuration.
Figure 5:
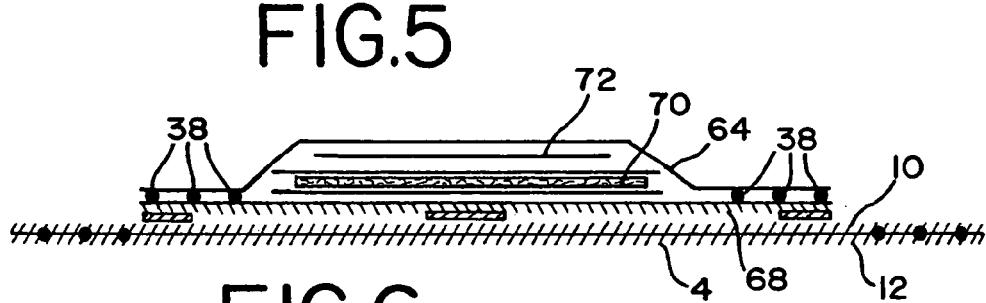
FIG. 5 is a schematic cross-sectional view taken along line 5—5 of FIGS. 2 and 3.
Figure 6:
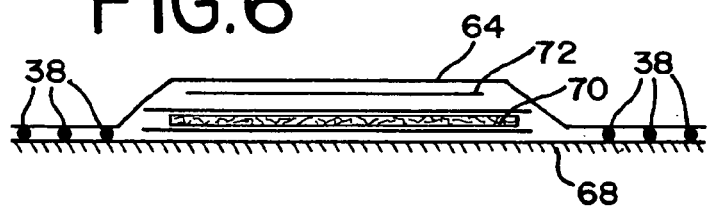
FIG. 6 is a schematic cross-sectional view taken along line 6—6 of FIGS. 2–4.

Referring to FIG. 1, it should be understood that the term "longitudinal," as used herein, means of or relating to length or the lengthwise direction 502, and in particular, the direction running between the front and back of the user. The term "laterally," as used herein means situated on, directed toward or running from side to side, and in particular, a direction 500 running from the left to the right of a user, and vice versa. The terms "upper," "lower" "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "body side," which means the side closest to the body of the user, while the terms "outer" and "lower" refer to a "garment side."

The term "body side" should not be interpreted to mean in contact with the body of the user, but rather simply means the side that would face toward the body of the user when the garment is applied to the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user when the garment is applied to the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, one web may be traveling along a first machine direction, which is substantially perpendicular to the travel of another web in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refer to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, or of one or more connected in-line pieces, and regardless of whether it may have non-continuous, discrete items disposed thereon, or is made up of connected non-continuous, discrete items.

Referring to FIGS. 1–3, an absorbent garment 2 includes a first, rear body panel 6 and a second, front body panel 4. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and/or abdomen. It should be understood that the first and second body panels can be discrete members, joined for example by an absorbent composite, or can be integrally formed as portions of a body chassis that has a front and rear body panel and a crotch portion extending therebetween.

In one preferred embodiment, shown in FIGS. 1–3, the first and second body panels each have an inner, body side surface 10 and an outer, garment side surface 12. The first, front body panel 4 has a length, which is measured between opposed first and second terminal edges 16 and 20, and which is preferably less than the overall length of the absorbent garment. Likewise, the second, rear body panel 6 has an overall length, which is measured between opposed first and second terminal edges 14 and 18, and which is also preferably less than the overall length of the absorbent garment. Each of the first and second body panels has an outboard edge 24, 28 formed along the outer periphery of laterally opposed side portions of the first and second body panel. It should be understood that the outboard edges of the front and rear body panels can be different lengths.

In one preferred embodiment, each of the first and second body panels includes a tapered edge 26 on each side thereof that forms in part the leg opening 125, along with the side edges of the absorbent composite 50. The tapered edge can be straight or curved. It should be understood that the first and second body panels can be configured without tapered side edges, such that the terminal edge of one or both of the first and second body panels extends across the entire lateral width of the body panel and forms part of the leg opening.

Referring to FIGS. 1–3, one or more, and preferably a plurality, meaning two or more, laterally extending elastic elements 36 are secured to each of the first and second body panels. In one preferred embodiment, a plurality of laterally extending elastic elements are longitudinally spaced across substantially the entire length of a waist portion of the front and rear body panels.

In one alternative preferred embodiment, one or both of the front and rear body panels has a "non-elasticized" area wherein there are no laterally extending elastic elements, or other elastic or elastomeric backing members, incorporated therein or making up any portion of the thickness or cross-section of the body panel at that area such that the material can be gathered by the elastic elements. Alternatively, the elastic elements can be "deactivated" to form the "non-elasticized" area. For example, the elastic elements can be severed, chopped or otherwise deactivated, for example by using a rotary die cutter, by melt-breaking (e.g. with a heated or ultrasonic function roll) or by any other means known to those skilled in the art. In one preferred embodiment, the deactivated area forms a landing zone along a body side of an outboard portion of the front body panel and underlies a landing member secured to the body side surface thereof.

Of course, it should be understood that the elastic elements can be spaced longitudinally along the entire length of the body panels, or along lesser lengths. The elastic elements can be oriented in a parallel, spaced apart relationship, or in a non-parallel relationship. For example elastic elements can extend along an upper waist portion and along the lower terminal edge defining the leg opening. It should be understood, that in an alternative embodiment, one or more separate waist bands, with or without elastic elements, can be secured to one or both of the rear and front body panels, preferably along the upper terminal edges thereof. Similarly, separate leg elastics can be secured along the edges of the body panels and absorbent composite that define the leg openings. Alternatively, one or both of the body panels can be formed without any elastic elements whatsoever.

In an alternative embodiment, shown in FIG. 4, an absorbent composite 50 extends longitudinally along the entire extent of the garment from one end 116 to the other end 118 thereof. A pair of front, side body panels 108 have inboard edges 180 that are secured to opposite side regions 186 of the absorbent composite, preferably on the body side of the body panels, adjacent one end of the absorbent composite and inboard from a peripheral side edge 52 of the absorbent composite. Likewise, a pair of rear, side body panels 110 have inboard edges 184 that are secured to opposite side regions 186 of the absorbent composite, preferably on the body side of the body panels, adjacent the opposite end of the absorbent composite and inboard from the peripheral side edge 52. The body panels 108, 110 extend laterally outward from the absorbent composite and form ear portions 112, 114 having outboard edges 188, 190 and tapered side edges 26. In this embodiment, the end portions of the absorbent composite connected to the side body panels 108, 110 also forms part of the front and rear body panels, as that term is defined above. The body panels 108, 110 preferably include elastic elements 36 in one of the configurations described above. Of course, the body panels can be configured without elastic elements. It should also be understood that the absorbent composite could alternatively be secured to the garment side of the body panels.

Referring to FIGS. 1–4, one or more leg elastic elements 38 can be secured along the edges of the body panels 4, 6, 108, 110 and the absorbent composite 50 to form a gasket with the leg of the user at the leg opening 125 formed by the absorbent garment. The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E. I. duPont De Nemours and Company, having an office in Wilmington, Del.

Each body panel, which forms part of a body chassis, is preferably formed as a composite, or laminate material, otherwise referred to as substrates or laminates, with the plurality of elastic strands 36, 38 sandwiched therebetween. Preferably two or more layers are bonded with various adhesives, such as hot melt, or by other techniques, including for example and without limitation ultrasonic bonding and heat pressure sealing. In one embodiment, the two layers are made of a nonwoven material. It should be understood that the body panels or chassis can be made of a single layer or substrate of nonwoven material, or can be comprised of more than two layers or substrates. Of course, it should be understood that other knitted or woven fabrics, elastomeric materials, nonwoven fabrics, polymer films, laminates and the like, composite elastic material, combinations thereof, and other suitable body chassis materials known to those skilled in the art, can be used to form one or more of the body panels, or body panel layers. For example, in one embodiment, the body panel is a laminate of a nonwoven and a film. The term "nonwoven" web or material, as used herein, means a web having a structure of individual fibers or filaments that are interlaid, but not in an identifiable manner and without the aid of textile weaving or knitting, as in a knitted or woven fabric. In one preferred embodiment, the body panels are made of a multiplicity of fibrous elongatable/retractable backing material including an orientable material having a dimensionally unstable state, a dimensionally stable state and a path of response along which said material has been retracted from the unstable state to the stable state.

As used herein the term "composite elastic material" refers to an elastic material which may be a multicomponent material or a multilayer material in which one layer is elastic. These materials may be, for example, "neck bonded" laminates, "stretch bonded" laminates, "neck-stretch bonded" laminates and "zero strain" laminates. "Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e.: the layers are joined together when only the non-elastic layer is in an extended condition. Such laminates usually have cross directional stretch properties. Examples of neck-bonded laminates are such as those described in U.S. Pat. Nos. 5,226,992, 4,981,747, 4,965,122 and 5,336,545 to Morman and U.S. Pat. No. 5,514,470 to Haffner et al., all of which are hereby incorporated herein by reference.

Conventionally, "stretch bonding" refers to a process wherein an elastic member is bonded to another member while only the elastic member is extended at least about 25 percent of its relaxed length. "Stretch bonded laminate" refers to a composite elastic material made according to the stretch bonding process, i.e.: the layers are joined together when only the elastic layer is in an extended condition so that upon relaxing the layers, the nonelastic layer is gathered. Such laminates usually have machine directional stretch properties and may be stretched to the extent that the nonelastic material gathered between the bond locations allows the elastic material to elongate. One type of stretch bonded laminate is disclosed, for example, by U.S. Pat. No. 4,720,415 to Vander Wielen et al., which is hereby incorporated by reference, and in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and 4,655,760 to Morman et al., all of which are hereby incorporated herein by reference.

"Neck-stretch bonding" generally refers to a process wherein an elastic member is bonded to another member while the elastic member is extended at least about 25 percent of its relaxed length and the other layer is a necked, nonelastic layer. "Neck-stretch bonded laminate" refers to a composite elastic material made according to the neck-stretch bonding process, i.e.: the layers are joined together when both layers are in an extended condition and then allowed to relax. Such laminates usually have omni-directional stretch properties.

"Zero strain" stretch bonding generally refers to a process wherein at least two layers are bonded to one another while in an untensioned (hence zero strain) condition and wherein one of the layers is stretchable and elastomeric and the second is stretchable but not necessarily elastomeric. Such a laminate is stretched incrementally through the use of one or more pairs of meshing corrugated rolls which reduce the strain rate experienced by the web. "Zero strain stretch laminate" refers to a composite elastic material made according to the zero strain stretch bonding process, i.e., the elastic and nonelastic layers are joined together when both layers are in an unextended condition and stretched though meshing corrugated rolls. The second layer, upon stretching of the laminate, will be at least to a degree permanently elongated so that the laminate will not return to its original undistorted condition upon release of the stretching force. This results in z-direction bulking of the laminate and subsequent elastic extensibility in the direction of initial stretching at least up to the point of initial stretching. Examples of such laminates and their production processes may be found in U.S. Pat. Nos. 5,143,679, 5,151,092, 5,167,897, and 5,196,000, all of which are hereby incorporated herein by reference.

In one embodiment, an outer cover, which extends from the front to back and includes a crotch portion, can form one layer or a portion of the body panels. The body panels and/or outercover can be extensible. In one preferred embodiment, the body panels and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The body panels and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

In one preferred embodiment of the body panels, the nonwoven layers or substrates, and also a landing material, can be made by spunbonding. Spunbond nonwoven webs or materials are made from melt-spun filaments or spunbonded fibers which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbound nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference.

The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. Pat. No. 5,707,468, which is hereby incorporated herein by reference in its entirety. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (m/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area.

Since the foraminous wire onto which the spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which the nonwoven materials are formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly(vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, which is hereby incorporated herein by reference, and which describes pattern-unbonded, or point un-bonded nonwoven fabrics having continuous bonded areas defining a plurality of discrete unbonded areas. Of course, it should be understood that the body panels could alternatively be made of pattern-unbonded nonwoven fabrics. In one embodiment, the calendar stack (not shown) includes an anvil roll and a pattern roll, which is heated and includes various raised landing portions. The raised portions of the pattern roll thermally bond the fibers to form the bonded areas. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In one alternative preferred embodiment, a landing material is secured to the body side surface of one or both of the front and rear body panels. In one preferred, the landing material is made of a point-unbonded nonwoven material, for example, a 2.0 osy point-unbonded material. One exemplary material of this type has been used in a HUGGIES® Ultratrim Disposable Diaper, which is commercially available from Kimberly-Clark Corporation. In another preferred embodiment, the landing material, which can be comprised of a portion of one of the body panel substrates, e.g., a body panel liner, is made of a nonwoven spunbond material, for example, a spunbond material having a basis weight of preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight nonwoven spunbond material exhibits strength and tear characteristics allowing it to be used as a body panel. Other materials that may be used as the nonwoven material include various meltblown materials, and also bonded-carded materials.

In other alternative embodiments, the landing material can be made of a loop material, which typically includes a backing structure and a plurality of loop members extending upwardly therefrom. The loop material can be formed by any suitable material, such as acrylic, nylon or polyester, and can be formed from such methods as warp knitting, stitch bonding or needle punching. Suitable loop materials are available from Guilford Mills, Inc., Greensboro, N.C., U.S.A. under the trade designation No. 36549.

The body panel 4, 6 nonwoven material is preferably substantially hydrophobic, which may optionally be treated with a surfactant or otherwise process to impart a desired level of wettability and hydrophilicity. In one particular embodiment of the invention, the body panel is a nonwoven, wireweave spunbond polypropylene fabric composed of about 1.6 denier fibers formed into a web having a basis weight of about 0.6 osy. One suitable nonwoven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIGS. 1–4, 7, 8 and 10, fastener members 42, 142 each include first and second portions 202, 204, 302, 304. In the embodiment of FIGS. 1, 2 and 4, the first and second portions 202, 204 are formed by folding a web 206 of fastener material to form a first and second fold 202, 204, which correspond to the first and second portions respectively, and a folded edge 208 joining the first and second folds.

Figure 8:
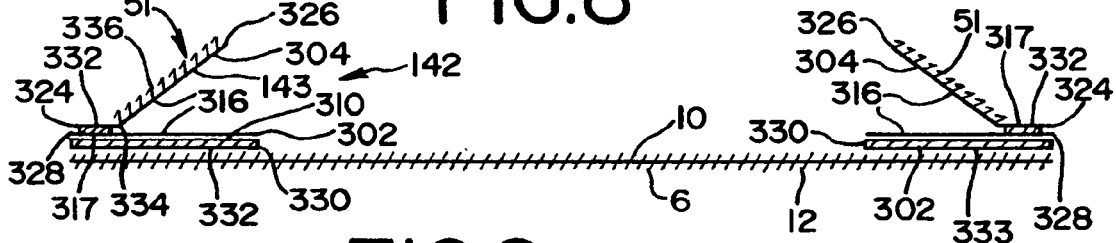
FIG. 8 is a schematic cross-sectional view taken along line 8—8 of FIG. 3.
Figure 9:
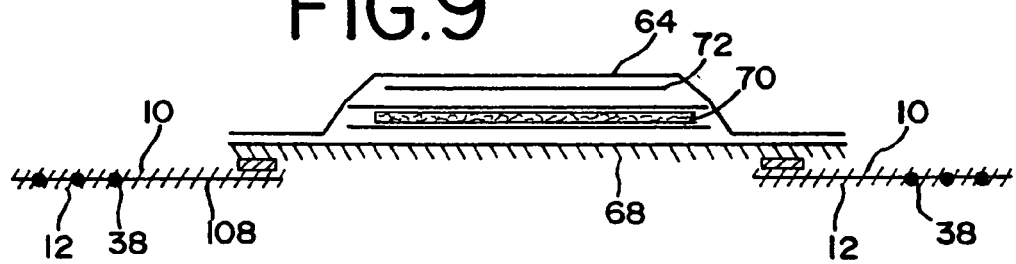
FIG. 9 is a schematic cross-sectional view taken along line 9—9 of FIG. 4.

Alternatively, as shown in FIGS. 3 and 8, the first portion 302 and the second portion 304 are formed as separate pieces, rather than being integrally formed from a single piece. In this preferred embodiment, an edge portion 317 of the second portion 304 is fixedly secured to the body side surface 310 of the first portion 302, with the garment side surface of the edge portion 317 attached to the body side surface of the first portion 310, and with the second portion 304 then folded such that a body side surface of the edge portion 317 faces the garment side surface 316 of the remainder of the second portion 304 when engaged with the front body panel. The garment side surface of the edge portion 317 and the body side surface of the first portion 302 can be joined by bonding, for example with a layer of adhesive 332, or other thermal, sonic, adhesive and other types of bonds known to those of skill in the art, or by various mechanical devices, including stitching, rivets, buttons, snaps and other known types of fastening devices.

Figure 13:
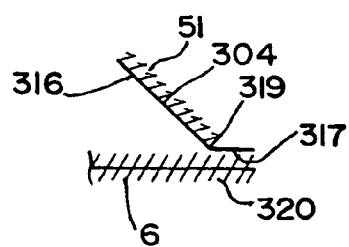
FIG. 13 is a partial cross-sectional view of one preferred embodiment of a fastener member and body panel.

Alternatively, as shown in FIG. 13, an outboard portion 320 of the rear body panel 6 defines the first portion, with the edge portion 317 of the second portion 304 being fixedly attached directly to the bodyside surface 10 of the rear body panel 6 without an additional first portion layer. Alternatively, the embodiment of FIG. 13 can be defined as having a first portion 317 having a garment side surface fixedly secured to the bodyside surface of the rear body panel and a hinged joint, or folded edge 319, connecting the first portion 317 to a second portion, defined as the remainder of the second portion 304. In this preferred embodiment, the hinged joint 319 is formed between an inboard edge of the first portion 317 and the outboard edge of the second portion 304.

Referring to FIGS. 1–4, 7, 8, 10 and 13, the second portion 204, 304 has an outboard edge 224, 324 and an inboard edge 226, 326. Likewise, the first portion has an outboard edge 228, 328, and in the embodiments of FIGS. 1–4, 7, 8 and 10, an inboard edge 230, 330. Preferably, the outboard edges 228, 328, 224, 324 of the first and second portions 202, 302, 204, 304 are hingedly connected. For example the outboard edges 224, 228 of the first and second portions 202, 204 form the folded edge 208. The term "hinge," as used herein, means a flexible joint that allows movement of one member relative to another, preferably about an axis, and can include living or virtual hinges, mechanical hinges or other types of devices permitting such movement. Likewise, the term "hingedly connected," as used herein, means that two or more members are flexibly connected at a joint such that at least one member can move relative to the other(s), preferably about an axis.

Figure 7:
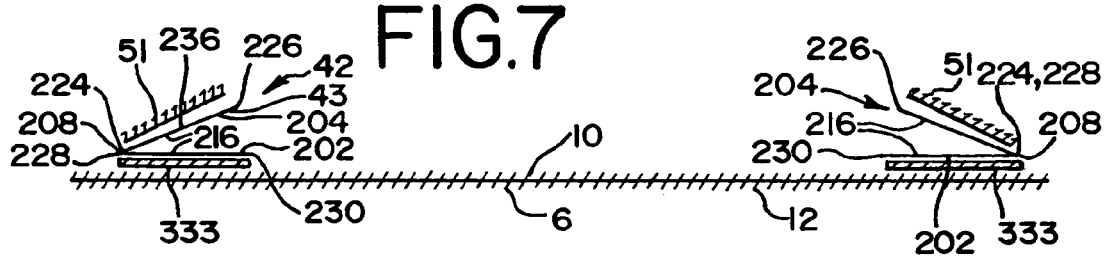
FIG. 7 is a schematic cross-sectional view taken along line 7—7 of FIG. 2.
Figure 10:
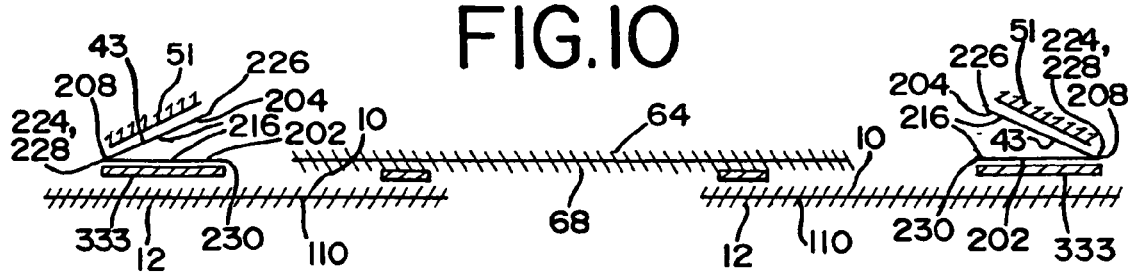
FIG. 10 is a schematic cross-sectional view taken along line 10—10 of FIG. 4.

It should be understood that the hinge, or hinged connection, between the first and second portions 202, 204 can be formed by the folded edge 208 between the portions, as shown for example and without limitation in FIGS. 7, 10 and 13, by a portion 334, 319 of one of the first and/or second portions bending or flexing or having a folded edge, as shown for example in FIG. 8, by an intervening joint, such as a bond 332, intervening piece of material or other known types of mechanical hinges, interposed between the first and second portions, or any other type of device known to those of skill in the art that permits such movement. In essence, the hinged connection allows the first portion 202, 302 to move relative to the second portion 204, 304, and vice versa, such that the second portion 204, 304 can be moved from a closed position, wherein the body side surface 216, 316 of the first and second portions 204, 304 are facing each other, preferably in contact, to an open position, wherein the body side surface of the first portion is not in contact with the body side surface of the second portion.

Referring to FIG. 1, the second portion of the fastener members 42 are releasably attached to the body side surface 10 of the front body panel 4, preferably along a side portion 35 thereof. In one embodiment, the side portion includes a deactivacted area or zone. The elastic elements in the body panel that are not deactivated allow the side portions to be stretched to provide a snug fit around the user. It should be understood that none of the elastic elements need be deactivated. In other embodiments, the front body panel, including the side portions, may not incorporate any elastic elements, or may incorporate a limited number spaced across various portions of the length thereof, as explained herein, so as to be placed to fit or conform to the user's body.

Referring to the embodiments illustrated in FIGS. 1–10, the first portions 202, 302 of the fastener members 42 are preferably fixedly secured to the body side surface 10 of the rear body panel 6, 110 and the second portions 204, 304 releasably engage the body side surface 10 of the front body panel 4, 108. The first portions 202, 302 can be fixedly secured to the rear body panel 6, 110, e.g., with adhesive bonds 333, sonic bonds, thermal bonds, pinning, stitching or other known types of attachment, which can be applied continuously or in various patterns. In a preferred embodiment, the side edges 24, 28, 188, 190 of the front and rear body panels are disposed proximate each other and substantially abut, but are not directly attached to one another to form a seam. Rather, the hinged joint 208, 334, 319 between the first and second portions of the fastener member bridge between the front and rear body panels to form a seamless, pant-type garment. Moreover, the front and rear body panels do not overlap, so as to thereby avoid a bulky appearance of the garment. In this way, the garment can be pulled on like a pant-type garment, but can thereafter be removed or adjusted as a refastenable garment. Moreover, the fastener member 42, 142 can be refastenably disengaged from the front body panel prior to putting the garment on. Once the "open" garment is positioned on the user, the fastener member 42, 142 can be refastenably engaged with the front body panel 4, 108 to secure the garment to the user.

In an alternative embodiment, the fastener members can be fixedly secured to the front body panel and releasably engage the rear body panel. In yet another alternative embodiment, the fastener members can be releasably engaged with both the front and rear body panels.

Preferably, the front body panel does not include a separate landing member secured thereto. Instead, the front body panel itself serves as a landing material. Alternatively, a landing member, preferably made of a landing material, including for example and without limitation a point-unbonded material or any other loop material or any material suited for engagement with an adhesive or tape, can be secured along the outboard edges on the body side surface of the body panel.

The garment is initially formed as a pant-type garment, with the fastener members 42, 142 joining the opposite side edges 24, 28, 188, 190 of the front and rear body panels 4, 6, 108, 110. During use, or even prior to application, the fastener members 42, 142 can be disengaged from the one or both of the front and rear body panels, if releasably secured thereto, so as to allow the garment to thereafter be removed or applied as a diaper-type garment.

In one alternative embodiment, an outer cover is disposed over the entire garment and forms the outer garment side layer or substrate of the front and rear body panels, with the various elastic elements 36, 38 disposed between a body side liner on each of the front and rear body panels, which liner preferably is configured as a single substrate, and the outer cover, which is also preferably configured as single substrate. In this way, the portion of the outer cover that overlies the front body panel liner and is fitted around the front of the user forms part of the front body panel, while the portion of the outer cover that overlies the rear body panel liner and is fitted around the rear of the user forms part of the rear body panel. The front and rear body panels, with the liners and with the outer cover forming portions thereof and preferably extending therebetween, forms a chassis. The outer cover is preferably made of a nonwoven material, similar to that of the other body panel materials described herein. It should be understood that the body panels, including the outer cover, can be configured with any number of a plurality of substrates, and that the body panels can include other layers and substrates.

Preferably, as shown in FIGS. 1–4, 7, 8 and 10, the first and second portions 202, 204, 302, 304 of the fastener members 42, 142 define a carrier member 43, 143. The carrier member, which comprises the first and second portions, can be made from any of the body panel materials described herein, including for example and without limitation a nonwoven material, such as a spunbond material or meltbond material, a woven material, a film, a nonwoven laminate, or combinations thereof, any of which can include various elastic elements or other elastomeric materials or laminates to provide it with various stretch characteristics. It should be understood that the first and second portions also can be made of different materials, especially when they are formed as separate discrete members. In addition, it should be understood that the fastener member can be made without a carrier member, e.g., wherein a hook material or tape material forms one or more of the first and second portions.

Although shown as rectangular, it should be understood that the fastener member 42, 142, and in particular the first and second portions 202, 204, 302, 304, can have other shapes, including various curvilinear contours and one more tab members. Preferably, the fastener members 42, 142, and the first and second portions 202, 204, 302, 304 thereof, have a length that is substantially the length of the side edges 24, 28, 188, 190 of the front and rear body panels 4, 6, 108, 110. Of course, it should be understood that the fastener member can have a lesser length, and extend along only a portion of the length of the side edges of the body panels.

In a preferred embodiment, the pair of fastener members 42, 142 used to releasably secure the front and rear body panels define a "fastening system," which refers to the grouping of fastener members used to releasably secure two or more portions of an absorbent garment. Although the fastening system is shown as being configured with two fastener members, it should be understood that it could include a single fastener member or additional fastener members, and that the two-fastener member fastening system shown in the Figures is meant to be illustrative rather than limiting. For example, the fastening system could include three, four or even more fastener members.

Referring to FIGS. 2–4, 7, 8 and 10, the second portion 204, 304 has a refastenable portion 51 formed or disposed on a garment side surface 236, 336 thereof. In an alternative embodiment, where the first portion is also releasably attached to the rear body panel, the first portion also includes a refastenable portion. The refastenable portion 51 preferably comprises an array of hooks, as explained below, but alternatively can comprise various tapes or adhesives, such as pressure sensitive adhesives, buttons, zippers, snaps and other releasable and reattachable fastening devices known in the art.

Preferably, the refastenable portion 51 extends along the entire length of the second portion 204, 304 and fastener member and along the entire width of the second portion 204, 304. Alternatively, the refastenable portion can have a length and width less then or greater than the length and width of the second portion, and can be configured, for example and without limitation, as one or more discrete patch members secured to the second portion. In yet another alternative embodiment, a plurality of refastenable portions are arrayed or positioned along the length of the fastener member, and in particular the second portion. Likewise, the refastenable portion 51 can have a width that is less than or greater than the width of the second portion 204, 304, and can include one or more discrete refastenable patches positioned across the width of the second portion. In one alternative embodiment, the refastenable portion is formed integrally with one or both of the first and second portions, and preferably with at least the second portion.

It should be understood that any of the various fastener member configurations, and refastenable configurations, described herein can be used interchangeably.

In one preferred embodiment, the refastenable portion 51 comprises a hook-type fastener member, or hook strip, which is secured to the carrier member 43, 143 and preferably the second portion 204, 304, with adhesive, ultrasonic bonding, stitching or other known attachment devices. In another embodiment, the entire fastener member 42, 142, including the first and second portions, is configured as a hook strip. In one embodiment, the hooks can be deadened along a portion of the garment side of the strip in the attachment location, such that the garment side can be fixedly secured to the body panel, if desired. Alternatively, the first and second portions can be releasably engaged with both the first and second body panels respectively.

It should be understood that the term "hook" as used herein means any element capable of engaging another element, and is not intended to limit the form of the engaging elements, for example to include only "hooks," but rather encompasses any form or shape of engaging element, whether unidirectional or bi-directional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn. Other examples of hook fasteners are the Velcro® HTH-851 and HTH-829 hook fasteners available from Velcro USA, Inc.

In one preferred embodiment, a mushroom-type hook strip comprises a homogeneous backing of thermoplastic resin and, integral with the backing, an array of upstanding stems distributed across at least one face of the backing, each having a mushroom head. The array of hooks on each strip comprise an engagement portion having a longitudinal length. The stems can have a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

The stems of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the hook strip makes them less likely to break during disengagement. When the hook strip is used with the nonwoven material herein described, the enhanced strength of the hooks makes them less likely to break under disengagement forces than the fibers of the material, a beneficial attribute for at least two reasons. First, broken hooks can create debris whereas a broken fiber typically does not. Second, the nonwoven material typically contains many more engageable fibers than there are hooks per unit area, thus allowing a greater number of disengagements before a hook-and-loop fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in one or more directions forming the fiber engaging portions. These fiber engaging portions extend outwardly from the stem portion at any angle so that they can project upwardly away from the film backing, parallel with the film backing or even downward toward the film backing.

For example, the hook head portion has a deformed fiber engaging portion that projects downward. Preferably, the lower surface of the fiber engaging portion also projects downward forming a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip makes it easier to firmly releasably engage nonwoven materials in shear, possibly because the many thin heads can easily move radially into engagement with rather small fibers. Thus the hook strip is particularly useful for hook-and-loop fastening when the "loops" are provided by nonwoven materials which are not particularly adapted for use as the loop portions of hook and loop fasteners, and which are not as well engaged by known prior art hook strips. For example, the hook strip is particularly well-suited for engaging the topographically flatter nonwoven materials described above, including the nonwoven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the nonwoven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratios preferably of from 1.5:1 to 12:1, and more preferably from 2.5:1 to 6:1.

For most uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, 143 and in a preferred embodiment the second portion 204, 304, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

The hook strip has a preferably substantially continuous planar backing of thermoplastic resin. Integral with the backing too many specs is the array of hooks projecting generally at right angles to one major surface of the backing. Each of the hooks has a stem, and, at the end of the stem opposite the backing, a generally circular plate-like cap or head projecting radially past or overhanging the stem so as to form a fiber engaging portion that projects downward. Preferably, the lower surface of the fiber-engaging portion also projects downward forming a crook between the lower face of the fiber engaging portion and the stem base portion. The stem can also have a fillet around its base.

When the absorbent garment is secured to the user, the fastener members 42, 142 are fixedly or releasably secured to the body side surface 10 of the rear body panels and is releasably engaged with the body side surface 10 of the front body panel 4, 108, or a landing member secured thereto. In particular, the heads on the hooks engage the fibers of the body panel, whether elasticized or not, or alternatively the landing material making up the landing member. The refastenable portions 51 can be initially engaged with the fibers to form a mechanical bond with the body panel or landing member during the manufacturing process so as to help maintain the connection between the side and middle portions.

In an alternative embodiment, the fastener member is a tape member with a refastenable portion formed as an adhesive, preferably a pressure sensitive adhesive. The tape member, which preferably has a non-stick body side surface, is preferably folded to form the first and second portions, or forms a first portion secured to a separate second portion. Alternatively, the tape member can be joined to a carrier member. A garment side of the second portion, or tape member, releasably engages the body side surface of the front body panel, or a landing member disposed thereon, either of which can be made of any of the materials described above, including various nonwoven materials and films.

Referring to FIGS. 1–6 and 9, the absorbent garment includes an absorbent composite 50 having first and second longitudinally opposed terminal end edges 60, 62. The absorbent composite preferably includes a substantially liquid permeable topsheet 64, or liner, and a substantially liquid impermeable backsheet 68, or outer cover. A retention portion 70 is disposed or sandwiched between the topsheet and the backsheet, which are connected. The topsheet, backsheet and other components of the absorbent composite 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent composite" refers to any material or assembly capable of absorbing liquids or bodily exudates, and may be comprised of a single material or component, for example a retention portion.

Additional layers, including for example, a surge layer 72, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite can further include one or more longitudinally extending barrier cuffs formed along the opposite lateral sides of the absorbent composite on the body side surface thereof.

The backsheet 68 is preferably fluid impermeable, but may be fluid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material that permits gases, such as water vapor, to escape from the absorbent garment while substantially preventing liquid exudates from passing through the backsheet. For example, the breathable backsheet may be composed of a microporous polymer film or a nonwoven fabric that has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 to Kellenberger for Absorbent Products Containing Hydrogels With Ability To Swell Against Pressure, U.S. Pat. No. 5,601,542 to Melius et al. for Absorbent Composite, and U.S. Pat. No. 5,651,862 to Anderson et al. for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIGS. 1–3, the opposite garment side of the end regions of the absorbent composite, and in particular, the outer, garment side surface of the backsheet 68, are secured to the body side surface of the longitudinally opposed crotch ends of the first and second body panels 4, 6, and in particular the liner portion of those body panels. Alternatively, and referring to FIG. 4, the absorbent composite 50 extends substantially the entire length of the absorbent garment and is secured to the body side surface 10 of body panels 108, 110 on each side thereof. It should be understood that the absorbent composite can be secured to the body panels using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween. In addition, it should be understood that the absorbent composite can be attached to the garment side surface of the body panels.

Figure 11:
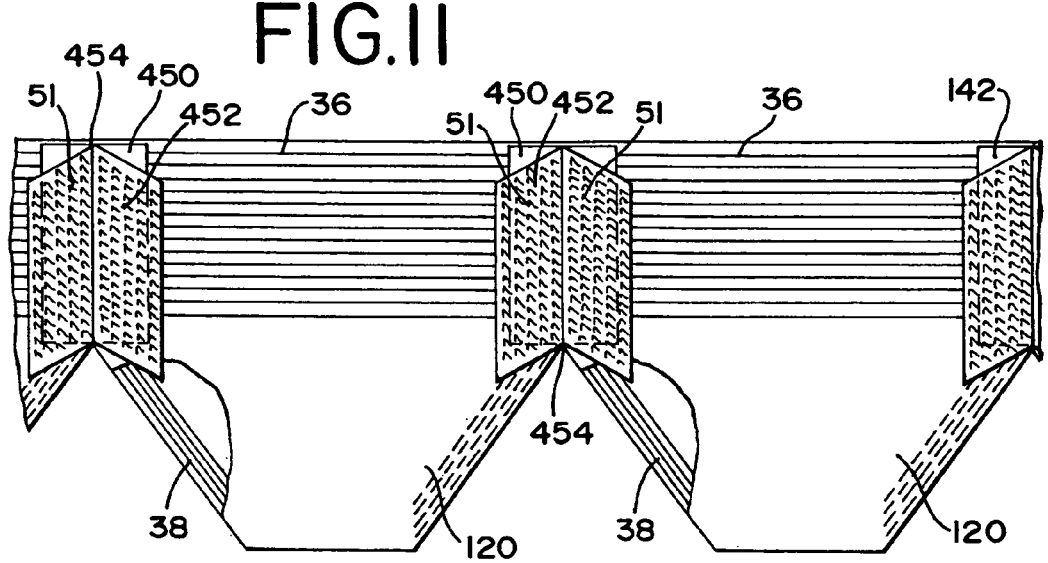
FIG. 11 is a partial schematic top view representation of a body panel web with a fastener member applied thereto.
Figure 12:
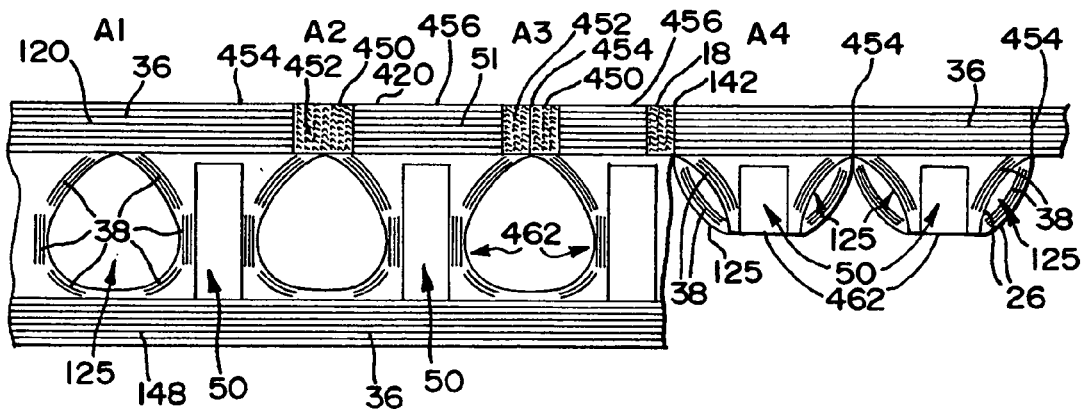
FIG. 12 is a partial schematic top view representation of one embodiment of a method of fabricating one embodiment of a refastenable absorbent garment.

Referring to FIGS. 11 and 12, various preferred methods for fabricating one or more embodiments of the aforedescribed refastenable absorbent garments are illustrated. Although the processes are described in terms of various zones, it should be understood that they are continuous processes.

Referring to FIGS. 11 and 12, a continuous first body panel web 120, which preferably forms the rear body panel, and which is preferably made of one or more of the materials described above, is moved along in the process in a machine direction. Alternatively, the continuous body panel web includes body panels intermittently connected to the absorbent composite, as shown for example in FIG. 4, so as to form a chain of material. Referring to FIG. 12, the rear body panel web 120 is secured to the absorbent composite 50, which is also secured to a continuous front body panel web 148 that forms the front body panel. Again, the continuous front body panel web can be formed from connected discrete pieces of body panels webs and the absorbent composite, which will be assembled to form the garment shown in FIG. 4.

In particular, the rear body panel web 120 moves along a path parallel to the front body panel web 148 in the machine direction. The absorbent composite 50, extending in the cross direction, is then applied to the body side of each of the front and rear body panel base webs 148, 120 to form a ladder type configuration, although it should be understood that the absorbent composite could be attached to the garment side of each body panel. Or, when manufacturing the embodiment shown in FIG. 4, the absorbent composite, in combination with the body panels, forms the ladder type configuration. The absorbent composite 50 can be assembled in a machine direction and can thereafter be rotated and applied to the front and rear body panel base webs, or applied thereto without rotation if the machine direction of the absorbent composite assembly is perpendicular to the machine direction of the garment assembly. The absorbent composite can be incorporated either before or after the assembly of the front and rear body panel webs. In one preferred embodiment, where the outer cover is secured to and forms part of the front and rear body panels and a crotch portion 462 of the absorbent garment, the absorbent composite 50 is applied to the body chassis after the outer cover and body panel liners are joined with the elastic elements disposed therebetween. The absorbent composite 50 is secured to the body panel base webs 120, 148 by bonding and the like, or by other devices known to those of skill in the art.

In one embodiment, where the front and rear body panel webs are separate from one another and from the absorbent composite, leg openings are formed between the successive cross direction absorbent composites, which define the crotch portions and which are spaced along the machine direction. In an alternative embodiment, where the outer cover defines in part the front and rear body panels, a die cutter successively cuts leg openings 125 in the outer cover between the absorbent composites to form the ladder type configuration with a plurality of crotch portions. The cutter can also shape one or both of the body panel webs.

A landing member, made of a landing material can be applied to the front body panel, preferably on the body side surface and along the side edges thereof, as it moves therewith in a machine direction. The landing material can be made of any of the above-described materials, including for example a point unbonded, nonwoven material or a spunbond nonwoven material, or elastically extendable materials with retraction. The landing material can also be made of various loop materials as described above. Alternatively, if the fastener member is configured as a tape, the landing material preferably made of various materials that interface with such tape.

Referring to FIG. 12 at zone A2 and to FIG. 11, in one preferred embodiment, a plurality of discrete first and second fastener pieces 450, 452 are successively applied to the body side surface of the rear body panel web 120 along the machine direction. Each first and second fastener piece includes a first and second end spaced along the machine direction. In particular, and referring to zone A3, the garment side surface of the first fastener piece 450 is fixedly secured, preferably by bonding, such as ultrasonic bonding, across its entire surface, to the body side surface of the rear body panel web 120. Alternatively, the garment side surface of the first fastener piece is releasably secured to the rear body panel web, by way of a refastenable portion.

Next, a body side surface of the second fastener piece 452 is fixedly secured, preferably by bonding, along a center region 454 thereof to the body side surface of the first fastener piece 452 along the center region thereof. The first and second fastener pieces can be bonded prior to applying the assembly thereof, and in particular the garment side of the first fastener piece, to the body panel web, or the second fastener piece can be secured to the first fastener piece simultaneously with securing the first fastener piece to the body panel web.

In one preferred embodiment, the second fastener piece includes a carrier material and a refastenable portion 51 disposed thereon, preferably along the entire garment side surface thereof, although a lesser area can be covered by the refastenable portion. In an alternative preferred embodiment, the second fastener piece 452 is configured entirely of a refastenable material, for example as a strip of refastenable material, having a refastenable portion, for example an array of hooks, formed on a first side thereof.

Referring to zone A4 of FIG. 12, the crotch portion 462 is folded such that the front body panel base web 148 overlies and faces the rear body panel base web 120. The body side surface of the front body panel base web 120 is releasably engaged with the garment side surface, and in particular the refastenable portion disposed thereon, of the second fastener piece 452. The front and rear body panel webs 120, 148 and first and second fastener pieces 450, 452 are then successively cut with a cutter along the cross direction at the center region 454 so as to form a plurality of discrete body panels 4, 6 and refastenable absorbent garments, with the front and rear body panels being refastenably connected with the fastener members. In an alternative embodiment, the front and rear body panels also can be cut before the crotch portion is folded. The cutter can be a knife and anvil cutter, a laser, or water jet cutter, or any other cutter known to those of skill in the art. Each of the pair of fastener members 42 formed from a first and second fastener piece 450, 452 are attached proximate to adjacent side edges 28, 190 of successive body panels 6, 110 and absorbent garments in the stream of such body panels and garments. In this embodiment, the absorbent product is formed as pant-type product, with the fastener members 142 folded over and releasably secured to the body side surface 10 of the front body panel. In use, the fastener members 142 can be disengaged from the front body panel, so as to allow the garment to be removed, or so as to adjust the fit thereof.

The lateral width of the fastener pieces 450, 452 can be shortened or lengthened to provide more or less adjust capability, as the side edge 24, 188 of the front body panel 4, 108 can be moved away from the side edge 28, 190 of the rear body panel 6, 110 while still releasably engaging the fastener member 142.

In one alternative embodiment, the first fastener piece is eliminated altogether. In this embodiment, the second fastener piece is secured directly to the body side surface of the rear body panel web along a center region of the second fastener piece, with the fastener piece having a refastenable portion formed on a garment side surface thereof. The front body panel web is then folded over the rear body panel web and is releasably engaged with the refastenable portion of the fastener piece. The body panel webs and fastener piece are then cut along the center region to form discrete absorbent garments, as shown for example in FIG. 13.

Referring to FIGS. 1, 2 and 4, in an alternative embodiment, wherein the fastener members 42 are made of a first portion 202 folded over a second portion 204, a garment side of the first portion 202 of the folded fastener member is simply applied to the body side surface of the rear body panel web 120, or after the web is cut, to the body side surface 10 of the rear body panel 6, 110. The crotch portion of the garment is then folded with the front body panel web 148 or, if the web is already cut, the front body panel 4, 108 releasably engaging the garment side surface of the second portion 204 of the fastener member.

Various aspects of the process for making the absorbent garment are further disclosed in U.S. application Ser. No. 09/834,870, filed Apr. 13, 2001, and entitled "Multiple Component Web," U.S. application Ser. No. 09/834,875, filed Apr. 13, 2001 and entitled "Method of Assembling Personal Care Absorbent Article," U.S. application Ser. No. 09/834,869, filed Apr. 13, 2001, and entitled "Pant-Type Personal Care Articles, and Methods of Making and Using Such Personal Care Articles," U.S. application Ser. No. 09/834,787, filed Apr. 13, 2001 and entitled "Methods of Changing Size of Pant-Type Personal Care Articles Outputted from a Manufacturing Process," and U.S. application Ser. No. 09/834,682, filed Apr. 13, 2001 and entitled "Passive Bonds For Personal Care Article," the entire disclosures of which are hereby incorporated by reference.

In other aspects, the absorbent garment and the process for making the absorbent garment are further disclosed in U.S. application Ser. No. 60/303,307, filed Jul. 5, 2001, and entitled "Refastenable Absorbent Garment," the entire disclosure of which is hereby incorporated by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A refastenable absorbent garment comprising:
   a first body panel having a body side and a garment side;
   a second body panel having a body side and a garment side; and
   a fastener member attached to said body side of said first body panel and comprising a refastenable portion formed on a garment side of said fastener member, said refastenable portion releasably attached to said body side of said second body panel, wherein said refastenable portion directly engages said second body panel, wherein said fastener member comprises a first portion attached to said body side of said first body panel and a second portion comprising said refastenable portion releasably attached to said body side of said second body panel, and wherein each of said first and second body panels comprise an outboard side edge and wherein each of said first and second portions comprise an inboard and an outboard edge, wherein said outboard edges of said first and second portions are positioned closer to said outboard side edges of said first and second body panels, respectively, than are said inboard edges of said first and second portions, and wherein said outboard edges of said first and second portions are hingedly connected.

2. The refastenable absorbent garment of claim 1 wherein said fastener member is fixedly attached to said body side of said first body panel.

3. The refastenable absorbent garment of claim 2 wherein said fastener member is bonded to said body side of said first body panel.

4. The refastenable absorbent garment of claim 3 wherein said fastener member is ultrasonically bonded to said body side of said first body panel.

5. The refastenable absorbent garment of claim 1 wherein said first portion of said fastener member is releasably attached to said body side of said first body panel.

6. The refastenable absorbent garment-of claim 1 wherein said first portion is bonded to said second portion.

7. The refastenable absorbent garment of claim 6 wherein said refastenable portion comprises an adhesive.

8. The refastenable absorbent garment of claim 1 wherein each of said first and second portions have a body side and a garment side, wherein said body sides of each of said first and second portions are in contact when said absorbent garment is in a folded configuration with said body sides of said first and second body panels in contact, and wherein said garment side of said first portion is attached to said body side of said first body panel and wherein said garment side of said second portion is releasably engaged with said body side of said second body panel.

9. The refastenable absorbent garment of claim 1 wherein said refastenable portion comprise an array of hook members.

10. The refastenable absorbent garment of claim 1 wherein said first body panel is a rear body panel and wherein said second body panel is a front body panel.

11. The refastenable absorbent garment of claim 1 wherein said first and second body panels are integrally formed as portions of a one-piece body chassis.

12. The refastenable garment of claim 1 wherein said fastener member does not directly or indirectly engage in any way said garment side of either of said first or second body panels.

13. A refastenable absorbent garment comprising:
   a first body panel having a body side and a garment side;
   a second body panel having a body side and a garment side; and
   a fastener member attached to said body side of said first body panel and comprising a refastenable portion formed on a garment side of said fastener member, said refastenable portion releasably attached to said body side of said second body panel, wherein said refastenable portion directly engages said second body panel, wherein said fastener member comprises a first portion attached to said body side of said first body panel and a second portion comprising said refastenable portion releasably attached to said body side of said second body panel, wherein said first and second portions comprise first and second folds hingedly connected along a folded edge.

14. A refastenable absorbent garment comprising:
  a first body panel having a body side, a garment side and an outboard side edge;
  a second body panel having a body side, a garment side and an outboard side edge; and
  a fastener member comprising first and second portions each having an inboard and an outboard edge, wherein said first portion is attached to said body side of said first body panel and said second portion is releasably attached to said body side of said second body panel, wherein said second portion directly engages said second body panel, and wherein said outboard edges of said first and second portions are hingedly connected, wherein said fastener member does not engage directly or indirectly in any way said garment side of either of said first or second body panels.

15. The refastenable absorbent garment of claim 14 wherein said first portion of said fastener member is fixedly attached to said body side of said first body panel.

16. The refastenable absorbent garment of claim 15 wherein said first portion of said fastener member is bonded to said body side of said first body panel.

17. The refastenable absorbent garment of claim 14 wherein said first portion of said fastener member is releasably attached to said body side of said first body panel.

18. The refastenable absorbent garment of claim 14 wherein said first and second body panels are integrally formed as portions of a one-piece body chassis.

19. A method for assembling a refastenable absorbent garment comprising:
  providing a first body panel having a body side and a garment side;
  providing a second body panel having a body side and a garment side;
  providing a fastener member comprising a first and second portion each having a body side and a garment side, wherein said body side of said first portion faces said body side of said second portion and wherein said first and second portions are hingedly connected;
  applying said garment side of said first portion of said fastener member to said body side of said first body panel; and
  releasably applying said body side of said second body panel directly to said garment side of said second portion of said fastener member, wherein each of said first and second body panels comprise an outboard side edge and wherein each of said first and second portions comprise an inboard and an outboard edge, wherein said outboard edges of said first and second portions are positioned closer to said outboard side edges of said first and second body panels, respectively, than are said inboard edges of said first and second portions, and wherein said outboard edges of said first and second portions are hingedly connected.

20. The method of claim 19 wherein applying said garment side of said first portion of said fastener member to said body side of said first body panel comprises fixedly securing said garment side of said first portion of said fastener member to said body side of said first body panel.

21. The method of claim 20 wherein said fixedly securing said garment side of said first portion of said fastener member to said body side of said first body panel comprising bonding said garment side of said first portion of said fastener member to said body side of said first body panel.

22. The method of claim 19 wherein applying said garment side of said first portion of said fastener member to said body side of said first body panel comprises releasably securing said garment side of said first portion of said fastener member to said body side of said first body panel.

23. The method of claim 19 wherein said first portion is bonded to said second portion.

24. The method of claim 19 wherein said first and second body panels are integrally formed as portions of a one-piece body chassis.

25. A method for assembling a refastenable absorbent garment comprising:
  providing a first body panel having a body side and a garment side:
  providing a second body panel having a body side and a garment side:
  providing a fastener member comprising a first and second portion each having a body side and a garment side, wherein said body side of said first portion faces said body side of said second portion and wherein said first and second portions are hingedly connected wherein said first and second portions comprise first and second folds hingedly connected along a folded edge;
  applying said garment side of said first portion of said fastener member to said body side of said first body panel; and
  releasably applying said body side of said second body panel directly to said garment side of said second portion of said fastener member.

26. A method for manufacturing a refastenable absorbent garment comprising:
  moving a first body panel web having a body side and a garment side in a machine direction;
  moving a second body panel web having a body side and a garment side in a machine direction;
  providing a plurality of fastener members each comprising a first and second portion, wherein said first and second portions each have a body side and a garment side;
  successively applying said garment side of said first portions of said fastener members to said body side of said first body panel web; and
  successively, releasably applying said body side of said second body panel web directly to said garment side of said second portions of said fastener members, wherein said successively applying said garment side of said first portions of said fastener members to said body side of said first body panel web and said successively, releasably applying said body side of said second body panel web directly to said garment side of said second portions of said fastener members comprises successively applying said garment side of said first portions of said fastener members to said body side of said first body panel web and successively, releasably applying said body side of said second body panel web directly to said garment side of said second portions of said fastener members without directly or indirectly engaging in any way said garment side of either of said first or second body panel webs with any portion of said fastener members.

27. The method of claim 26 wherein each of said plurality of said first and second fastener members comprises a center region, and further comprising successively securing said center region of said first portions of said fastener members to said center region of said second portions of said fastener members, and successively cutting said first and second body panel webs and said first and second portions along said center regions of said first and second fastener members to form a plurality of discrete absorbent garments.

28. The method of claim 27 wherein said successively securing said center region of said first portions of said fastener members to said center region of said second portions of said fastener members comprises successively bonding said center region of said first portions of said fastener members to said center region of said second portions of said fastener members.

29. The method of claim 26 wherein said successively applying said garment side of said first portions of said fastener members to said body side of said first body panel web comprises successively bonding said garment side of said first portions of said fastener members to said body side of said first body panel web.

30. The method of claim 26 wherein said successively applying said garment side of said first portions of said fastener members to said body side of said first body panel web comprises successively releasably securing said garment side of said first portions of said fastener members to said body side of said first body panel web.

31. The method of claim 26 wherein said second portions of said fastener members each comprise an array of hooks, and wherein successively, releasably applying said body side of said second body panel web to said garment side of said second portions of said fastener members comprises successively, releasably engaging said body side of said second body panel web with said array of hooks.

32. The method of claim 31 wherein said second body panel comprises a landing material defining at least in part said body side thereof.

33. The method of claim 26 wherein said second portions of said fastener members each comprise an adhesive patch, and wherein successively, releasably applying said body side of said second body panel web to said garment side of said second portions of said fastener members comprises successively, releasably engaging said body side of said second body panel web with said adhesive patch.

34. The method of claim 26 wherein said first and second body panels are integrally formed as portions of a one-piece body chassis.

35. A method of using an absorbent garment comprising:
providing said absorbent garment comprising a first body panel having a body side and a garment side, a second body panel having a body side and a garment side, and a fastener member attached to said body side of said first body panel and comprising a refastenable portion formed on a garment side of said fastener member, said refastenable portion releasably attached directly to said body side of said second body panel, wherein said fastener member comprises a first portion attached to said body side of said first body panel and a second portion comprising said refastenable portion releasably attached to said body side of said second body panel, and wherein each of said first and second body panels comprise an outboard side edge and wherein each of said first and second portions comprise an inboard and an outboard edge, wherein said outboard edges of said first and second portions are positioned closer to said outboard side edges of said first and second body panels, respectively, than are said inboard edges of said first and second portions, and wherein said outboard edges of said first and second portions are hingedly connected;
applying said garment to a user; and
disengaging said fastener member from said body side of said second body panel
providing a fastener member attached to said body side of said first body panel and comprising a refastenable portion formed on a garment side of said fastener member, said refastenable portion releasably attached to said body side of said second body panel, wherein said refastenable portion directly engages said second body panel.

36. The method of claim 35 further comprising releasably reengaging said fastener member with said body side of said second body panel.

37. The method of claim 35 wherein said fastener member comprises a first portion attached to said body side of said first body panel and a second portion releasably attached to said body side of said second body panel, wherein said first and second portions are hingedly connected.

38. A method for assembling a refastenable absorbent garment comprising:
providing a first body panel having a body side and a garment side;
providing a second body panel having a body side and a garment side;
providing a fastener member comprising a first and second portion each having a body side and a garment side, wherein said body side of said first portion faces said body side of said second portion and wherein said first and second portions are hingedly connected;
applying said garment side of said first portion of said fastener member to said body side of said first body panel; and
releasably applying said body side of said second body panel directly to said garment side of said second portion of said fastener member; wherein said applying said garment side of said first portion of said fastener member to said body side of said first body panel and said releasably applying said body side of said second body panel directly to said garment side of said second portion of said fastener member comprises applying said garment side of said first portion of said fastener member to said body side of said first body panel and releasably applying said body side of said second body panel directly to said garment side of said second portion of said fastener member without directly or indirectly engaging in any way said garment side of either of said first or second body panels with any portion of said fastener member.

* * * * *